United States Patent
Amano et al.

(10) Patent No.: US 6,544,966 B1
(45) Date of Patent: Apr. 8, 2003

(54) AGENTS PROMOTING LAMININ PRODUCTION IN SKIN CELLS

(75) Inventors: Satoshi Amano, Yokohama (JP); Toshio Nishiyama, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/647,506
(22) PCT Filed: Mar. 26, 1999
(86) PCT No.: PCT/JP99/01540
§ 371 (c)(1), (2), (4) Date: Sep. 29, 2000
(87) PCT Pub. No.: WO99/49832
PCT Pub. Date: Oct. 7, 1999

(30) Foreign Application Priority Data

Mar. 31, 1998 (JP) .......................................... 10-101910
Dec. 4, 1998 (JP) .......................................... 10-345677

(51) Int. Cl.[7] ...................... A61K 31/685; A61K 31/66
(52) U.S. Cl. .......................................... 514/78; 514/114
(58) Field of Search .................................. 514/78, 114

(56) References Cited

U.S. PATENT DOCUMENTS 5,723,136 A * 3/1998 Tanaka et al.

FOREIGN PATENT DOCUMENTS

| JP | 62-29507 | 2/1987 |
| JP | 8-67621 | 3/1996 |
| JP | 8-104647 | 4/1996 |
| JP | 10029911 | * 2/1998 |
| JP | 10-147515 | 6/1998 |

OTHER PUBLICATIONS

Shinji et al., skin activator hacing glycosaminoglycan . . . , Patent abstract of Japan, JP 08067620, Mar. 1996.(previouly enclosed PTO–892;see paper No. 4).*
Tanaka et al., "Rizorin shishitsu ni yoru hifu no hiaruron san sansei sokushin kouka (I)", Journal of Japan Oil Chemists' Society, vol. 46, No. 9 (1997), pp. 969–975.
Tanaka et al., "Rizorin shishitsu ni yoru hifu no hiaruron san sansei sokushin kouka (II)", Journal of Japan Oil Chemists' Society, vol. 46, No. 9 (1997), pp. 977–984.
Shinji et al., skin activator hacing glycosaminoglycan . . . , Patent abstract of Japan, JP 08067620, Mar. 1996.*
Shinji et al., skin activator hacing glycosaminoglycan . . . , Patent abstract of Japan, JP 08067619, Mar. 1996.*
Shinji et al., Effects of lysophospholipids on hyaluronic acid . . . , abstract, Nihon Yukagakkaishi, 1997, vol. 46(9), pp. 977–984.*

* cited by examiner

Primary Examiner—Marianne C. Seidel
Assistant Examiner—Vickie Kim
(74) Attorney, Agent, or Firm—Wenderoth, Lind & Ponack, L.L.P.

(57) ABSTRACT

Disclosed are compositions for promoting the production of laminin 5 in epidermic cells which contain a lysophospholipid having a $C_{14-22}$ fatty acid residue or a preparation derived from soybeans as an active ingredient and which can be used in the fields of cosmetics and dermatology. These compositions may be used especially for the purpose of potentiating the skin.

3 Claims, No Drawings

AGENTS PROMOTING LAMININ PRODUCTION IN SKIN CELLS

TECHNICAL FIELD

This invention relates to agents for promoting the production of laminin 5 in epidermic cells and skin potentiating compositions useful in the fields of cosmetics and dermatology. More particularly, this invention relates to the use of specific lysophospholipids and soybean-derived preparations for the purpose of potentiating skin functions through the medium of the promotion of laminin 5 production in epidermic cells.

BACKGROUND ART

In the fields of cosmetics and dermatology, a wide variety of means have been proposed and tried to mitigate or cure the damage of the skin due to the influence of an external environment (e.g., exposure to sunlight) and aging. For example, main skin changes caused by aging include wrinkle formation, hardening and reduced elasticity.

In connection with the causes of such changes, chief interest is directed not to the epidermis of the skin, but rather to the functions of collagen fibers and elastic fibers consisting of collagen and glycosaminoglycans and present in the dermis forming the substratum of the epidermis. As means for preventing or correcting such changes, the use of a hydroxycarboxylic acid (e.g., Japanese Patent No. 2,533, 339) and the use of a lysophospholipid [Japanese Patent Laid-Open No. 67621/'96 or Journal of Japan Oil Chemists' Society, Vol. 46, No. 9 (1997), pp. 13–19] have been proposed. In the former patent, it is suggested that the stratum corneum and wrinkles can be exterminated by preventing a loss of collagen fibers. On the other hand, it is suggested in the latter patent that lysophospholipids enhance the ability of human fibroblasts to produce a glycosaminoglycan (specifically, hyaluronic acid) and hence exhibit a skin beautifying effect. It is also suggested that lysophospholipids exert little influence on the synthesis of collagenous protein in skin fibroblasts (see the aforementioned Journal of Japan Oil Chemists' Society).

In the year 1991, laminin 5 was discovered by Dr. Burgeson (Rousselle et al., J. Cell Biol., 114, 567, 1991). Subsequently, the presence of an autoimmune disease to laminin 5 (Fine et al., J. Am. Acad. Dermatol., 24, 119, 1991) and a serious disease caused by the genetic deficiency of laminin 5 (Aberdam et al., Nat. Genet., 6, 299, 1994) was discovered. In this disease, the formation of blisters was observed at the dermal-epidermal junction, revealing that laminin 5 is an indispensable component for the adhesion of them. It is known that compounds of the laminin family are synthesized in various types of cells. Among them, laminin 5 is a principal component of the structure (called the basement membrane) located at the dermal-epidermal junction, and composed of various glycoproteins and proteoglycans. Moreover, laminin 5 has an activity for promoting the adhesion of epidermic cells and thereby functions to bind epidermic cells directly to the basement membrane (Rousselle et al., J. Cell Biol., 114, 567, 1991). Furthermore, it is also known that the adhesion of epithelial cells to the basement membrane components is important in maintaining their cellular function (Schmidhauser et al., Proc. Natn. Acad. U.S.A., 87, 9, 118, 1990). Furthermore, in the skin of old persons, duplication of the basement membrane (Lavker et al., J. Invest. Dermatol., 73, 59, 1979) and a thickening of the basement membrane and a decrease of IV type collage constituting it (Vazquez, Maturitas, 25, 209, 1996) have been reported. Thus, there seems to be a possibility that structural changes of the basement membrane may be responsible for hypofunction of the skin in old persons.

As to Japanese Patent Laid-Open No. 67621/'96 and Journal of Japan Oil Chemists' Society, Vol. 46, No. 9 (1997), pp. 13–19, the latter more specifically explains the contents of the former with the aid of additional experimental data. According to the latter (i.e., the aforementioned Journal of Japan Oil Chemists' Society), it is suggested that, among the lysophospholipids represented by the formula

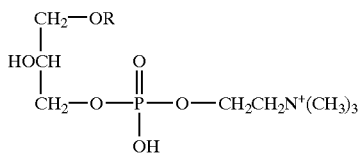

the compound in which R is a $C_{12}$ saturated fatty acid residue promotes the above-described production of hyaluronic acid, but the compounds in which R is a $C_{14}$ or higher saturated fatty acid residue inhibits its production strongly.

DISCLOSURE OF THE INVENTION

On the basis of the above-described findings, the present inventors have searched for substances capable of improving the function of the skin on the assumption that the firm binding of epidermic basal cells to the basement membrane is essential for the manifestation of normal skin functions and that it is more important to promote the production of laminin 5 in the corium and the like, rather than the production of collagen and hyaluronic acid.

As a result, the present inventors have now found that, in contrast to the aforementioned Journal of Japan Oil Chemists' Society suggesting that the compounds of the above formula in which R is a $C_{14}$ or higher saturated fatty acid residue strongly inhibits the production of hyaluronic acid in human skin fibroblasts, the compounds of the above formula in which R is a $C_{14-22}$ fatty acid residue optionally having up to six unsaturated double bonds, and soybean-derived preparations that are likely to contain such compounds or their precursors, are more effective in promoting the above-described production of laminin 5 and thereby potentiating the skin.

Accordingly, the present invention relates to a composition for promoting the production of laminin 5 in epidermic cells which contains a compound of the following formula (I) or a mixture of two or more such compounds, as an active ingredient.

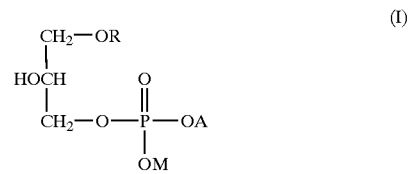

wherein R is a $C_{14-22}$ fatty acid residue optionally having up to six unsaturated double bonds, A is a hydrogen atom or a —$CH_2CH_2N^+(CH_3)_3$ group, and M is a hydrogen atom or an alkali metal atom, but is a hydrogen atom when A is a —$CH_2CH_2N^+(CH_3)_3$ group.

In other embodiments, the present invention relates to a method for promoting the production of laminin 5 in epidermic cells by administering the composition to the skin of a mammal, and the use of a compound of the following formula (I) as an active ingredient of a composition for promoting the production of laminin 5.

In further embodiments, the present invention also relates to a composition for promoting the production of laminin 5 which contains a soybean-derived preparation that is likely to contain a compound of the above formula (I) or its precursor, as an active ingredient, a method for promoting the production of laminin 5 in epidermic cells by administering the composition to the skin of a mammal, and the use of the soybean-derived preparation as an active ingredient of a composition for promoting the production of laminin 5.

DETAILED DESCRIPTION OF THE INVENTION

According to the present invention, the compounds of the above formula (I) wherein R is a $C_{14-22}$ fatty acid residue, which may strongly inhibit the production of hyaluronic acid in human skin fibroblasts as suggested in the aforementioned Journal of Japan Oil Chemists' Society, and soybean-derived preparations that are likely to contain such compounds, can be effectively used especially for the purpose of promoting the production of laminin 5 and/or potentiating the skin through the medium of such action.

The mammals in which it is contemplated to promote the production of laminin 5 and/or potentiate the skin through the medium of such action according to the present invention include, but are not limited to, human beings, pet animals (e.g., dogs, cats, rats and guinea pigs) and domestic animals (e.g., cattle, pigs and sheep).

The compounds of the above formula (I), which are used in the present invention, are compounds known generically as lysophospholipids. These compounds may be directly or indirectly obtained from a wide variety of biological sources, but may also be chemically synthesized.

R in the above formula (I) is a radical selected from among $C_{14-22}$ fatty acid residues (acyl groups). Specifically, these acyl groups include residues derived from saturated fatty acids such as myristic acid ($C_{14}$), pentadecanoic acid ($C_{15}$), palmitic acid ($C_{16}$), margaric acid ($C_{17}$), stearic acid ($C_{18}$), nonadecanoic acid ($C_{19}$), arachidic acid ($C_{20}$), heneicosanoic acid ($C_{21}$) and behenic acid ($C_{22}$). Of these, the preferred residues are those derived from $C_{14}$, $C_{16}$, $C_{18}$, $C_{20}$ and $C_{22}$ saturated fatty acids which are abundantly found especially in biological sources. Moreover, from the viewpoint of activity for promoting the production of laminin 5, the residues derived from $C_6$ and $C_{18}$ saturated fatty acids are preferred.

Furthermore, R can be an acyl group comprising any of the above-described fatty acid residues in which up to six unsaturated double bonds are present. The positions and number of double bonds in such fatty acid residues should preferably correspond to those in the fatty acid residues of phospholipids or lysophospholipids obtainable from biological sources. However, no limitation is placed thereon, so long as the number of double bonds is six or less and is not contrary to the purpose of the present invention. Among the fatty acids forming such acyl groups, oleic acid ($C_{18}$: (Z)-9-octadecenoic acid), elaidic acid ($C_{18}$: (E)-9-octadecenoic acid), linolic acid ($C_{18}$: 9,12-octadecadienoic acid), α-linolenic acid ($C_{18}$: 9,12,15-octadecatrienoic acid), β-linolenic acid ($C_{18}$: 6,9,12-octadecatrienoic acid), 5,8,11-icosatrienoic acid ($C_{20}$), 5,8,11,14-eicosatetraenoic acid ($C_{20}$), 4,8,12,15,19-docosapentaenoic acid ($C_{22}$) and 4,7,10,13,16,19-docosahexaenoic acid ($C_{22}$) are especially preferred.

A in formula (I) can be a hydrogen atom or a $-CH_2CH_2N^+(CH_3)_3$ group. When A is the former, the compound is the so-called lysophosphatidic acid, and when A is the latter, the compound is the so-called lysophosphatidylcholine. In the case of lysophosphatidic acid, it may be in the form of a salt in which M in formula (I) is an alkali metal. Preferred examples of this alkali metal include potassium, sodium and lithium.

In the present invention, the above-described compounds of formula (I) may be used alone or in a mixture of two or more. Such mixtures may be formed by combining two or more compounds in which R is any of the above-described preferred groups. Alternatively, a lysophosphatidylcholine mixture may be prepared by obtaining a phospholipid from a biological source [in particular, seeds of the soybean (Glycine max Merril)], hydrolyzing it with phospholipase $A_2$ known per se to form a lysophospholipid, hydrolyzing it with phospholipase D or by chemical means as required, and purifying it, and may be used as such. Such lysophosphatidylcholine mixtures include, for example, Reagent Lysolecithin Prepared from Soybeans (Wako Pure Chemical Industries Ltd.; Catalog No. 120-00832), Lysolecithin Kyowa (Iwase Cosfa Co., Ltd.), Sunlecithin WL-25 (Taiyo Chemical Industry Co., Ltd.), Blendmax (Central Soya) and LIPIDURE NC-22 (Nippon Oil & Fats Co., Ltd.), which may be used as such or, if necessary, after further purification.

Alternatively, a soybean-derived preparation which has not necessarily been hydrolyzed or purified as described above, but can promote the production of laminin 5, may be used as the active ingredient of the present invention. Such soybean-derived preparations include ground soybeans as such, and extracts obtained by extracting ground soybeans with a suitable solvent. Such extracts include, but are not limited to, ones obtained by extraction with a water-containing lower alcohol, lower alcohol, lower alkyl ketone, lower alkyl ether, polyhydric alcohol or a mixture of two or more such solvents.

Specific examples of useful water-containing lower alcohols include methanol, ethanol, isopropanol and n-propanol containing less than 50% by weight, preferably 5 to 40% by weight, of water; specific examples of useful lower alcohols include methanol, ethanol, isopropanol, n-propanol, n-butanol and, sec-butanol, containing essentially no water; and specific examples of useful lower alkyl ketones include acetone, methyl ethyl ketone, butyl methyl ketone and isobutyl methyl ketone.

Specific examples of useful di-lower alkyl ethers include diethyl ether, di-isopropyl ether, di-n-propyl ether, di-n-butyl ether, n-butyl methyl ether and n-butyl ethyl ether; and specific examples of useful lower alkyl esters of carboxylic acids include ethyl acetate and butyl acetate.

Specific examples of useful polyhydric alcohols include 1,3-butanediol, propylene glycol, glycerol and diglycerol.

Moreover, there may also be used preparations obtained by extracting soybeans with an extraction solvent selected from hydrocarbons such as cyclohexane, toluene and xylene; and halogenated hydrocarbons such as dichloromethane and dichloroethane, so long as they meet the purpose of the present invention.

Soybeans or ground soybeans are extracted with a solvent as described above according to any of various per se known methods, and the resulting extract is used, either as such or after drying it and redissolving it in a suitable solvent, to measure its activity for the production of laminin 5 as will be described later. Thus, the preparation used in the present invention can be selected. The extraction may be carried out according to any of various procedures commonly employed in solid-liquid extraction, for example, by soaking optionally dried soybeans or ground soybeans in any of the above-described solvents and allowing it to stand or shaking it on a shaker. Although the extraction temperature may be suitably chosen according to the solvent system used, it usually ranges from 5° C. to the boiling point of the solvent used and preferably up to 60° C. As to the extraction time, the optimum condition for the preparation used in the present invention may vary according to the solvent used and the temperature. However, it would be easy for those skilled in the art to determine the extraction time by measuring the activity for the production of laminin 5 as will be described layer.

The preferred extraction procedure comprises using 70 to 95% methanol or ethanol (having a water content of 30 to 5% and, if necessary, adjusted to pH 3–8), absolute methanol, absolute ethanol, acetone and diethyl ether or 1,3-butanediol, or propylene glycol, and soaking soybeans or ground soybeans therein at room temperature (i.e., 15 to 30° C.) to extract desired components. The extract thus obtained may be used in the present invention, either as such or after being further diluted with ethanol, or the dried extract may be used in the present invention, either as such or after being redissolved in ethanol.

Commercially available, typical examples of such soybean-derived preparations include soybean saponin [Saponin, Prepared from Soybeans; Wako Pure Chemical Industries Ltd., Tokyo (Catalog No. 190-08852)] and soybean lecithin [Lecithin, Prepared from Soybeans; Wako Pure Chemical Industries Ltd., Tokyo (Catalog No. 120-00832)].

The target cells for the present invention are different from the target cells for the above-described production of hyaluronic acid. Moreover, as specified by formula (I), the compounds intended for use in the present invention have not necessarily the same usable range or effective concentration as the compounds used for promoting the production of hyaluronic acid.

According to the present invention, there is provided a skin potentiating composition which contains, as an active ingredient, a compound of the above formula (I) or a mixture of two or more such compounds, or a preparation derived from soybeans, at a concentration sufficient to promote the production of laminin 5 in epidermic cells. The expression "skin potentiating" means to improve hypofunction of the skin associate, for example, with structural changes of the basement membrane due to aging or the like, more specifically, wrinkled skin and hardened skin.

The aforesaid "concentration sufficient to promote the production of laminin 5" may vary according to the type of the compound of formula (I) or soybean-derived preparation used, other ingredients used to prepare the composition, the dosage form of the composition, and its application time. Accordingly, the optimum concentration of a compound of formula (I) or a mixture of such compounds needs to be determined for each given composition. It would be easy for those skilled in the art to determine the optimum concentration by referring to this specification (in particular, the examples which will be given later) and carrying out a small-scale experiment as required.

However, when a compound of formula (I) or a mixture of such compounds is used, its concentration may generally be in the range of 0.0001 to 60% by weight, preferably 0.01 to 60% by weight, based on the total weight of the composition. On the other hand, when a soybean-derived preparation is used, its optimum amount used may generally vary according to the method of preparation from soybeans and, therefore, cannot be critically defined. However, when an extract obtained by extracting dry ground soybeans with water-containing methanol or ethanol or with a mixture of ethanol or acetone and diethyl ether is used as the preparation, its content on a dry solid basis may be in the range of 0.0001 to 20% by weight based on the total weight of the composition.

The composition of the present invention, which has been prepared in the above-described manner, can promote the production of laminin 5 in the skin by administering it topically to a mammal (e.g., by applying it to the skin). The topical administration may be carried out several times a day or at regular intervals (e.g., at intervals of several days) according to the intended purpose. The frequency of administration and the amount of active ingredient administered at a time can be determined with consideration for the results of tests on experimental animals as will be described later, or the results of the actual use in volunteers (because the compositions of the present invention exhibit essentially no toxicity to mammals).

Moreover, especially when the active ingredient comprises a compound of formula (I), the compositions of the present invention may be administered orally or parenterally.

The skin potentiating compositions of the present invention may take various forms such as an aqueous solution, an oil solution, other solutions, a milky lotion, cream, gel, a suspension, microcapsules, powder, granules, capsules and a solid. After they are made into these forms according to the per se known methods, the resulting preparations including lotions, milky lotions, creams, ointments, plasters, poultices, aerosols, injections, internal preparations (i.e., tablets, powders, granules, pills, syrups, troches, etc.), suppositories and the like may be applied to, sticked on, sprayed on, injected into, drunk into, or inserted into the body. Among these preparations, external preparations for the skin such as lotions, milky lotions, creams, ointments, plasters, poultices and aerosols are considered to be dosage forms suitable for the compositions of the present invention. The above-described "external preparations for the skin" include drugs, quasi drugs and cosmetics, and the same shall apply hereinafter.

The compositions of the present invention may suitably contain excipients and other additives (e.g., perfumes) which are commonly used in the preparation of such compositions, as well as fats and oils, surfactants, antiseptics, sequestering agents, water-soluble polymers, thickeners, powder ingredients, ultraviolet protectants, humectants, active ingredients, antioxidants, pH regulators, detergents, desiccants, emulsifiers and the like. When these various ingredients are incorporated into the skin potentiating compositions of the present invention, they must be added to such an extent as not to detract from the desired effects of the present invention.

The aforesaid fats and oils include liquid oils, solid fats, waxes, hydrocarbon oils, higher fatty acids, higher alcohols, synthetic ester oils and silicones.

Specifically, useful liquid oils include avocado oil, camellia oil, evening primrose oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, Chinese tung oil, Japanese tung oil, jojoba oil, germ oil, triglycerol, glycerol trioctanoate, glycerol triisopalmitate and the like; useful solid fats include cacao butter, coconut oil, horse fat, hardened coconut oil, palm oil, beef tallow, mutton tallow, hardened beef tallow, palm kernel oil, lard, beef bone fat, haze kernel oil, hardened oil, beef foot fat, neat's foot oil, Japan wax, hardened castor oil and the like; useful waxes include beeswax, candelilla wax, cotton wax, carnauba wax, bayberry wax, Chinese wax, spermaceti, montan wax, rice bran wax, lanolin, kapok wax, lanolin acetate, liquid lanolin, sugarcane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol ester, POE hydrogenated lanolin alcohol ether and the like; and useful hydrocarbon oils include liquid paraffin, ozokerite, squalane, pristane, paraffin, ceresine, squalene, vaseline, microcrystalline wax and the like.

Useful higher fatty acids include, for example, lauric acid, myristic acid, palmitic acid, stearic acid, behenic acid, oleic acid, 12-hydroxystearic acid, undecylenic acid, tallic acid, isostearic acid, linolic acid, linoleic acid, eicosapentaenoic acid (EPA) and docosahexaenoic acid (DHA).

Useful higher alcohols include, for example, straight-chain alcohols such as lauryl alcohol, cetyl alcohol, stearyl alcohol, behenyl alcohol, myristyl alcohol, oleyl alcohol and cetostearyl alcohol; and branched-chain alcohols such as monostearyl glycerol ether (batyl alcohol), 2-decyltetradecynol, lanolin alcohol, cholesterol, phytosterol, hexyldodecanol, isostearyl alcohol and octyldodecanol.

Useful synthetic ester oils include, for example, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid esters, N-alkyl glycol monoisostearate, neopentyl glycol dicaprate, diisostearyl malate, glycerol di-2-heptylundecanoate, trimethylolpropane tri-2-ethylhexylate, trimethylolpropane triisostearate, pentaerythritol tetra-2-ethylhexylate, glycerol tri-2-ethylhexylate, trimethylolpropane triisostearate, cetyl 2-ethylhexanoate, 2-ethylhexyl palmitate, glycerol trimyristate, tri-2-heptylundecanoic acid glyceride, castor oil fatty acid methyl ester, oleyl oleate, cetostearyl alcohol, acetoglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-hexyldecyl succinate, ethyl acetate, butyl acetate, amyl acetate and triethyl citrate.

Useful silicones include chain polysiloxanes such as dimethyl polysiloxane, methyl phenyl polysiloxane and methyl hydrogen polysiloxane; cyclic polysiloxanes such as decamethyl polysiloxane, dodecamethyl polysiloxane and tetramethyl tetrahydrogen polysiloxane; silicone resin having a three-dimensional network structure; silicone rubber; and the like.

Since the compounds of formula (I) which are used in the present invention have surface activity in themselves, it is usually unnecessary to use a surfactant. However, depending on the type of the composition, other anionic surfactants, cationic surfactants, ampholytic surfactants and nonionic surfactants may be used in combination with them.

Useful anionic surfactants include, for example, fatty acid soaps such as soap stock, sodium laurate and sodium palmitate; higher alkyl sulfuric ester salts such as sodium lauryl sulfate and potassium lauryl sulfate; alkyl ether sulfuric ester salts such as POE lauryl sulfate triethanolamine salt and POE lauryl sulfate sodium salt; N-acyl sarcosine salts such as sodium lauroyl sarcosine; higher fatty acid amide sulfonate salts such as sodium N-myristoyl N-methyltaurine, sodium coconut oil fatty acid methyltauride and sodium lauryl methyltauride; phosphoric ester salts such as sodium POE oleyl ether phosphate and POE stearyl ether phosphate; sulfosuccinic acid salts such as sodium di-2-ethylhexyl sulfosuccinate, sodium monolauroyl monoethanolamide polyoxyethylene sulfosuccinate and sodium lauryl polypropylene glycol sulfosuccinate; alkyl-benzenesulfonic acid salts such as linear dodecylbenzenesulfonic acid sodium salt, linear dodecylbenzenesulfonic acid triethanolamine salt and linear dodecylbenzenesulfonic acid; N-acylglutamic acid salts such as monosodium N-lauroyl glutamate, disodium N-stearoyl glutamate and monosodium N-myristoyl L-glutamate; higher fatty acid ester sulfate salts such as hardened coconut oil fatty acid glycerol sulfate sodium salt; sulfated oils such as Turkey red oil; and POE alkyl ether-carboxylic acids, POE alkyl allyl ether-carboxylic acid salts, α-olefinsulfonic acid salts, higher fatty acid estersulfonic acid salts, secondary alcohol sulfuric ester salts, higher fatty acid alkylolamide sulfuric ester salts, sodium lauroyl monoethanolamide succinate, N-palmitoylaspartic acid ditriethanolamine salt and sodium caseinate.

Useful cationic surfactants include, for example, alkyltrimethylammonium salts (e.g., stearyltrimethylammonium chloride and lauryltrimethylammonium chloride), dialkyldimethylammonium salts (e.g., distearyldimethylammonium chloride), poly(N,N'-dimethyl-3,5-methylenepiperidinium) chloride, alkylpyridinium salts (e.g., cetylpyridinium chloride), alkyl quaternary ammonium salts, alkyldimethylbenzylammonium salts, alkylisoquinolinium salts, dialkylmorpholinium salts, POE alkylamines, alkylamine salts, polyamine fatty acid derivatives, benzalkonium chloride and benzethonium chloride.

Useful ampholytic surfactants include, for example, imidazoline type ampholytic surfactants such as 2-undecyl-N,N,N-(hydroxyethylcarboxymethyl)-2-imidazoline sodium salt and 2-cocoyl-2-imidazolinium hydroxide-1-carboxyethyloxy disodium salt; and betaine type surfactants such as 2-heptadecyl-N-carboxymethyl-N-hydroxyethylimidazolinium betaine, lauryl dimethylaminoacetate betaine, alkyl betaines, amido-betaines and sulfobetaines.

Useful lipophilic nonionic surfactants include, for example, sorbitan fatty acid esters such as sorbitan mono-oleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; polyglycerol fatty acid esters such as glycerol mono (cottonseed oil fatty acid) ester, glycerol monoerucate, glycerol sesquioleate, glycerol monostearate, glycerol α,α'-oleate pyroglutamate, and glycerol malate; propylene glycol fatty acid esters such as propylene glycol monostearate; hardened castor oil derivatives; glycerol alkyl ethers; and polyoxyethylene-methylpolysiloxane copolymers.

Useful hydrophilic nonionic surfactants include, for example, POE sorbitan fatty acid esters such as POE sorbitan mono-oleate, POE sorbitan mono-stearate, POE sorbitan mono-oleate and POE sorbitan tetraoleate; POE sorbitol fatty acid esters such as POE sorbitol monolaurate, POE sorbitol penta-oleate and POE sorbitol monostearate;

POE glycerol fatty acid esters such as POE glycerol monostearate, POE glycerol monoisostearate and POE glycerol triisostearate; POE fatty acid esters such as POE monooleate, POE distearate, POE dioleate and ethylene glycol distearate; POE alkyl ethers such as POE lauryl ether, POE behenyl ether, POE 2-octyldodecyl ether and POE cholestanol ether; POE alkylphenyl ethers such as POE octylphenyl ether, POE nonylphenyl ether and POE dinonylphenyl; Pluronic type surfactants such as Pluronic; POE-POP alkyl ethers such as POE-POP cetyl ether, POE-POP 2-decyltetradecyl ether, POE-POP monobutyl ether, POE-POP hydrogenated lanolin and POE-POP glycerol ether; tetraPOE-tetra-POP ethylenediamine condensates such as Tetronic; POE castor oil or POE hardened castor oil derivatives such as POE castor oil, POE hardened castor oil, POE hardened castor oil monoisostearate, POE hardened castor oil triisostearate, POE hardened castor oil monoglutamate monoisostearate and POE hardened castor oil maleate; POE beeswax lanolin derivatives such as POE sorbitol beeswax; alkanolamides such as coconut oil fatty acid diethanolamide, lauric acid monoethanolamide and fatty acid isopropanolamides; and POE propylene glycol fatty acid esters, POE alkylamines, sucrose fatty acid esters, POE nonylphenylformaldehyde condensate, alkylethoxydimethylamine oxides and trioleyl phosphate.

The aforesaid antiseptics include methylparaben, ethylparaben, butylparaben and the like.

The aforesaid sequestering agents include edetic acid sodium salt, EDTA and the like.

The aforesaid water-soluble polymers include natural polymers, semisynthetic polymers, synthetic polymers and inorganic polymers.

Useful natural water-soluble polymers include polymers of vegetable origin, such as gum arabic, tragacanth gum, galactan, guar gum, carob gum, karaya gum, carrageenan, tamarind gum, xanthane gum, pectin, agar, quince seed (marmelo), algae colloid (brown algae extract), starches (made from rice, corn, potatoes and wheat) and glycyrrhizic acid; polymers of microbial origin, such as xanthane gum, dextran, succinoglucan and pullulan; polymers of animal origin, such as collagen, casein, albumin and gelatin; and the like.

Useful semisynthetic water-soluble polymers include starch-based polymers such as dextrin, carboxymethylstarch and methylhydroxypropylstarch; cellulose-based polymers such as methylcellulose, nitrocellulose, ethylcellulose, methylhydroxy-propylcellulose, hydroxyethylcellulose, cellulose sulfate dimethyl-dialkyl (12–20)ammonium, hydroxypropylcellulose, carboxymethyl-cellulose sodium (CMC), crystalline cellulose and powdered cellulose; alginic acid-based polymers such as sodium alginate and alginic acid propylene glycol ester; and the like.

Useful synthetic water-soluble polymers include vinyl polymers such as polyvinyl alcohol, polyvinyl methyl ether, polyvinyl pyrrolidone, carboxyvinyl polymer and alkyl-modified carboxyvinyl polymers; polyoxyethylene polymers such as polyethylene glycols 2000, 4000 and 6000; polyoxyethylene-polyoxypropylene copolymers; acrylic polymers such as sodium polyacrylate, polyethylene acrylate and polyacrylamide; polyethyleneimine; cationic polymers; and the like.

Useful inorganic water-soluble polymers include bentonite, magnesium aluminum silicate, laponite, hectorite, silicic acid anhydride and the like.

The aforesaid powder ingredients include inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metallic salts of tungstic acid, magnesium, silica, zeolite, barium sulfate, burned calcium sulfate (calcined gypsum), calcium phosphate, fluorapatite, hydroxyapatite, ceramic powders, metallic soaps (e.g., zinc myristate, calcium palmitate and aluminum stearate) and boron nitride; organic powders such as powdered polyamide resins (powdered nylons), powdered polyethylene, powdered polymethyl methacrylate, powdered polystyrene, powdered styrene-acrylic acid copolymer resin, powdered benzoguanamine resin, powdered polytetrafluoroethylene and powdered cellulose; inorganic white pigments such as titanium dioxide and zinc oxide; inorganic red pigments such as iron oxide (red oxide) and iron titanate; inorganic brown pigments such as β-iron oxide; inorganic yellow pigments such as yellow iron oxide and ochre; inorganic black pigments such as black iron oxide, carbon black and lower titanium oxides; inorganic violet pigments such as manganese violet and cobalt violet; inorganic green pigments such as chromium oxide, chromium hydroxide and cobalt titanate; inorganic blue pigments such as ultramarine blue and Prussian blue; pearl pigments such as titanium oxide-coated mica, titanium oxide-coated bismuth oxychloride, titanium oxide-coated talc, colored titanium oxide-coated mica, bismuth oxychloride and pearl essence; metal powder pigments such as aluminum powder and copper powder; organic pigments such as zirconium, barium and aluminum lakes including Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, Red No. 3, Red No. 104, Red No. 106, Red No. 227, Red No. 230, Red No. 401, Red No.505, Orange No. 205, Yellow No. 4, Yellow No. 5, Yellow No. 202, Yellow No. 203, Green No. 3 and Blue No. 1; natural pigments such as chlorophyll and β-carotene; and coloring materials such as Titan Yellow, carthamin and Safflor Red.

The aforesaid ultraviolet protectants include both "ultraviolet absorbers" which are substances capable of absorbing ultraviolet light chemically, and "ultraviolet screeners" which are substances capable of scattering and reflecting ultraviolet light by physical action.

Specifically, useful long-wavelength ultraviolet light (UVA) absorbers include anthranilic acid type ultraviolet absorbers such as methyl anthranilate and homomenthyl-N-acetyl anthranilate; benzophenone type ultraviolet absorbers such as 2,4-dihydroxybenzophenone, 2,2-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salts, 4-phenylbenzophenone, 2-ethylhexyl-4'-phenylbenzophenone-2-carboxylate, 2-hydroxy-4-n-octoxybenzophenone and 4-hydroxy-3-carboxybenzophenone; benzotriazole type ultraviolet absorbers such as 2,2'-hydroxy-5-methylphenylbenzotriazole, 2-(2'-hydroxy-5'-t-octylphenyl) benzotriazole and 2-(2'-hydroxy-5'-methyl-phenyl) benzotriazole; dianisoylmethane and 4-methoxy-4'-t-butyl-dibenzoylmethane; and the like.

Among these long-wavelength ultraviolet light absorbers, 4-methoxy-4'-tert-butyldibenzoylmethane, 2-hydroxy-4-methoxybenzophenone and 2-hydroxy-4-methoxybenzophenone derivatives (e.g., 2-hydroxy-4- methoxybenzophenone-5-sulfonic acid salts) are preferred long-wavelength ultraviolet light absorbers having excellent stability and effectiveness.

Useful medium-wavelength ultraviolet light (UVB) absorbers include benzoic acid type ultraviolet absorbers such as p-aminobenzoic acid (hereinafter referred to as PABA), PABA mono-glyceryl ester, N,N-dipropoxyPABA ethyl ester, N,N-diethoxyPABA ethyl ester, N,N-dimethylPABA ethyl ester, N,N-dimethylPABA butyl ester and N,N-dimethylPABA amyl ester; salicylic acid type ultraviolet absorbers such as dipropylene glycol salicylate, ethylene glycol salicylate, myristyl salicylate, methyl salicylate, amyl salicylate, menthyl salicylate, homomenthyl salicylate, octyl salicylate, phenyl salicylate, benzyl salicylate and p-isopropanolphenyl salicylate; cinnamic acid type ultraviolet absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-p-dimethoxycinnamate, octyl methoxycinnamate, 3-methyl-4-[methyl-bis(trimethylsiloxy)silyl]butyl 3,4,5-trimethoxycinnamate and mono-ethyl p-dimethoxycinnamate; camphor derivatives such as 3-(4'-methylbenzylidene)-d, 1-camphor, 3-benzylidene-d, 1-camphor and 5-(3,3-dimethyl-2-norbornylidene)-3-pentyn-2-one; and urocanic acid, ethyl urocanate, 2-phenyl-5-methylbenzoxazole, dibenzalazine and the like.

Moreover, useful ultraviolet screeners include titanium oxide ($TiO_2$), talc ($MgSiO_2$), carmine ($FeO_2$), bentonite, kaolin, zinc oxide (ZnO) and the like.

The aforesaid humectants include, for example, polyethylene glycol, propylene glycol, glycerol, 1,3-butylene glycol, hexylene glycol, xylitol, sorbitol, maltitol, chondroitin sulfate, hyaluronic acid, mucoitin sulfate, charonin sulfate acid, atelocollagen, cholesteryl 12-hydroxystearate, sodium lactate, bile acid salts, dl-pyrrolidonecarboxylic acid salts, short-chain soluble collagen, diglycerol (EO)PO adduct, Rosa roxburghii extract, yarrow extract and melilot extract.

The aforesaid active ingredients include whitening agents such as arbutin, vitamin C and its derivatives, kojic acid, placental extract, glutathione and strawberry gerenium extract; anti-inflammatory agents such as glycyrrhizic acid derivatives, glycyrrhetic acid derivatives, salicylic acid derivatives, hinokitiol, zinc oxide and allantoin; activators such as royal jelly, photosensitizers, cholesterol derivatives and calf blood extract; blood circulation promoters such as nonylic acid vanillylamide, benzyl nicotinate, β-butoxyethyl nicotinate, capsaicin, gingerone, cantharis tincture, ichthammol, caffeine, tannic acid, α-borneol, tocopheol nicotinate, inositol hexanicotinate, cyclandelate, cinnarizine, tolazoline, acetylcholine, verapamil, cepharanthine and γ-oryzanol; antiseborrheic agents such as sulfur and thianthol; substances effective for various purposes, such as phellodedron bark extract components, coptidis rhizome extract components, lithospermum root extract components, peony root extract components, swertia herb extract components, birch extract components, sage extract components, loquat extract components, ginseng extract components, aloe extract components, mallow extract components, iris extract components, grape extract components, coix seed extract components, sponge gourd extract components, lily extract components, saffron extract components, cnidium rhizome extract components, zingiberis rhizome extract components, syoorengyo extract components, petty white-root extract components, rosemary extract components, garlic extract components, thyme extract components, capsicum extract components, citrus unshiu peel and Japanese angelica root; vitamin A compounds such as retinol and retinol acetate; vitamin $B_2$ compounds such as riboflavin, riboflavin butyrate and flavin adenine dinucleotide; vitamin $B_6$ compounds such as pyridoxine hydrochloride and pyridoxine dioctanoate; vitamin C compounds such as L-ascorbic acid, L-ascorbic acid dipalmitate, L-ascorbic acid 2-sulfate sodium salt, L-ascorbic acid phosphate and DL-α-tocopherol-L-ascorbic acid diphosphate dipotassium salt; pantothenic acid compounds such as calcium pantothenate, D-pantothenyl alcohol, pantothenyl ethyl ether and acetylpentothenyl ethyl ether; vitamin D compounds such as ergocalciferol and cholecarciferol; nicotinic acid compounds such as nicotinic acid, nicotinic acid amide and benzyl nicotinate; vitamin E compounds such as α-tocopherol, tocopherol acetate, DL-α-tocopherol nicotinate and DL-α-tocopherol succinate; and other vitamins such as vitamin P and biotin.

As to these active ingredients, they may be extensively compounded into the compositions of the present invention, so long as the desired effects of the present invention are not detracted from thereby.

Since the compositions of the present invention, which have been prepared in the above-described manner, promote the production of laminin 5 in human epidermic cells, they can prevent hypofunction of the skin associated especially with structural changes of the basement membrane, and can promote the potentiation of the skin.

The present invention is more specifically explained with reference to the following examples. However, these examples are not to be construed to limit the scope of the invention.

Tests for the Ability to Produce Laminin 5
(1) Culture of Epidermic Stratum Corneum Cells Epidermic stratum corneum cells were isolated from the human preputium and cultured in an epidermic cell growth medium (KGM) having a low calcium concentration. To this culture medium were added bovine pituitary extract and EGF. After the cells were cultured in KGM up to the fourth generation, and treated with trypsin and EDTA to suspend adherent cells. Then, the culture was filtered to remove cell aggregates and thereby obtain a homogeneous cell suspension. The cells were collected by centrifugation and resuspended in DMEM-F12 (2:1)-0.1% BSA so as to give a cell density of $8 \times 10^4$ per ml. 0.5 ml each of this cell suspension was added to 0.5 ml of the same medium containing a twofold concentration of each test sample. Using a 24-well plate, incubation was carried out at 37° C. for 24 hours. After completion of the incubation, the culture supernatant was transferred to an Eppendorf tube and centrifuged at 15,000 rpm for 5 minutes. The supernatant was transferred to a new tube and stored at −20° C. till the day for the determination of laminin 5. In order to solubilize laminin 5 in the cells and bound to the culture plastics, a tris-HCl buffer (pH 7.4) containing various surfactants was added to each well and allowed to stand at −20° C. overnight. On the following day, the mixture was ultrasonicated and frozen again. On the following day, the mixture was thawed again and centrifuged at 15,000 rpm for 5 minutes. The supernatant was transferred to a tube and stored at −20° C. till the day for the determination of laminin 5.

(2) Determination of Laminin 5 by the Sandwich ELISA Method

Laminin 5 present in the culture supernatant and the cell layer was determined by the sandwich ELISA method. A monoclonal antibody (BM165) to the laminin α3 chain of laminin 5 was attached to a solid layer of a 96-well ELISA plate. In order to measure laminin 5 in a sandwiched manner, a monoclonal antibody (6F12) to the laminin β3 chain was previously biotinized (b-6F12) and used as the other antibody. In this method, only the heterotrimer (α3β3γ2) which can exhibit its function was measured, and the heretodimer (β3γ2) was not detected. A sample was added to each of the wells in which a 3% gelatin-phosphate buffer solution containing b-6F12 had previously been placed. The final degree of dilution of the sample in the wells was 1/4 for the culture medium and 1/10 for the cell layer. After the antigen-antibody reaction was carried out at 37° C. for 2 hours, the wells were washed, and an avidin HRP (horseradish peroxidase) solution was added thereto and reacted for a period of 30 minutes to 1 hour. After washing, a solution of ABTS serving as a substrate for HRP was added thereto and the absorbance at 405 nm was measured with an ELISA plate reader. A calibration curve was constructed over a range of 0 to 40 ng/ml.

The yield of laminin 5 was expressed by the sum of the amount liberated into the culture medium and the amount remaining in the cell layer.

(3) Results

The results are shown in Tables I and II below.

TABLE I

Effect of Lysophosoholipids on the Production
of Laminin 5 in Epidermic Stratum Corneum Cells (Comparative tests)

| Sample | Concentration (%) | Yield of laminin 5 (ng) Mean ± Standard deviation |
|---|---|---|
| Control with no addition | 0 | 40.3 ± 0.5 |
| Fetal calf serum | 1 | 98.8 ± 4.0 |
|  | 5 | 135.4 ± 3.5 |

(The present invention)

| Sample | Concentration (μg/ml) | Relative yield of laminin 5 based on control with no addition (%) Mean ± Standard deviation |
|---|---|---|
| LPC-C12: 0*[1] | 5 | 88.6 ± 5.1 |
| LPC-C14: 0 | 5 | 100.8 ± 5.6 |
| LPC-C16: 0 | 5 | 104.5 ± 3.3 |
| LPC-C18: 0 | 5 | 112.4 ± 8.0 |
| LPC-C18: 1 | 5 | 112.7 ± 6.7 |
| " | 50 | 147.4 ± 5.2 |
| LPC-C18: 2 | 5 | 133.6 ± 1.3 |
| " | 50 | 174.0 ± 5.4 |
| LPA-C18: 1 | 5 | 225.4 ± 12.5 |
| " | 50 | 254.0 ± 8.7 |
| Lecithin WL-25 | 5 | 158.3 ± 14.4 |
| " | 50 | 170.0 ± 15.1 |
| Kyowa Lysolecithin | 5 | 130.6 ± 4.7 |
| " | 50 | 140.5 ± 4.7 |
| LIPIDURE | 1 | 144 ± 4.8 |
| LIPIDURE | 10 | 163.2 ± 21.0 |
| LIPIDURE | 100 | 240.8 ± 14.2 |

*[1]For comparative purposes
In this table, LPC represents lysophosphatidylcholine.
In the expression "C12: 0" , "12" means the number of carbon atoms contained in R in formula (I), and "0" represents the number of unsaturated double bonds. The same shall apply to other cases.
LPA represents lysophosphatidic acid.

5 μg/ml of LPC corresponds to about 10 μM. As to the samples for which the yield of laminin 5 is shown only at a concentration 5 μg/ml they may exhibit an inhibitory effect when used at a high concentration of 50 μg/ml.

TABLE II

Effect of Soybean-derived Preparations on the Production
of Laminin 5 in Epidermic Stratum Corneum Cells
(The present invention)

| Sample | Concentration (%) | Yield of laminin 5 (ng) Mean ± Standard deviation |
|---|---|---|
| Control with no addition | 0 | 36.7 ± 6.0 |
| Soybean saponin*[2] | 0.0001 | 43.9 ± 3.2 |
|  | 0.001 | 77.3 ± 3.6 |
|  | 0.01 | 122.1 ± 3.0 |
| Control with no addition | 0 | 46.2 ± 6.4 |
| Soybean lecithin*[3] | 0.0001 | 51.8 ± 3.2 |
|  | 0.001 | 69.3 ± 2.6 |
|  | 0.01 | 97.1 ± 2.4 |

*[2] and *[3]: These samples were obtained from Wako Pure Chemical Industries Ltd., Tokyo, as "Saponin, Prepared from Soybeans" and "Lecithin, Prepared from Soybeans", respectively.

It can be seen from Tables I and II that the lysophospholipids and soybean-derived preparations in accordance with the present invention are effective in promoting the production of laminin 5 to an extent equal to or greater than fetal calf serum which is known to have a cell potentiating effect.

PREPARATION EXAMPLES

Preparation Example 1: Cream

| | |
|---|---|
| Polyoxyethylene (20 mole addition) cetyl alcohol ether | 1.0 |
| Methyl phenyl polysiloxane (20 cs) | 2.0 |
| Liquid paraffin | 3.0 |
| 2-Hydroxy-4-methoxybenzophenone | 5.0 |
| Soybean lysolecithin (Reagent Lysolecithin; manufactured by Wako Pure Chemical Industries Ltd.) | 0.2 |
| Propylene glycol | 5.0 |
| Glycerol | 2.0 |
| Ethyl alcohol | 15.0 |
| Carboxyvinyl polymer | 0.3 |
| Hydroxypropyl cellulose | 0.1 |
| 2-Aminomethylpropanol | 0.1 |
| Antiseptic | q.s. |
| Perfume | q.s. |
| Ion-exchanged water | q.s. |

(Preparation Method)

To ion-exchanged water were added propylene glycol, glycerol, ethyl alcohol, carboxyvinyl polymer, hydroxypropyl cellulose and 2-aminomethylpropanol. This mixture was adjusted to 70° C. by heating (aqueous phase).

Methyl phenyl polysiloxane, liquid paraffin, polyoxyethylene cetyl alcohol ether, an antiseptic, 2-hydroxy-4-methoxybenzophenone, soybean lysolecithin and a perfume were mixed. This mixture was adjusted to 70° C. (oily phase).

The aqueous phase was slowly added to the oily phase so as to pre-emulsify this mixture. After the emulsified particles were made uniform by means of a homomixer, the resulting emulsion was deaerated and cooled to obtain a cream.

Preparation Example 2: Cream

| | |
|---|---|
| Polyoxyethylene (20 mole addition) cetyl alcohol ether | 1.0 |
| Methyl phenyl polysiloxane (20 cs) | 2.0 |

-continued

| | |
|---|---|
| Liquid paraffin | 3.0 |
| 2-Hydroxy-4-methoxybenzophenone | 5.0 |
| Lysophosphatidic acid (LPA-C18: 1) | 0.2 |
| Propylene glycol | 5.0 |
| Glycerol | 2.0 |
| Ethyl alcohol | 15.0 |
| Carboxyvinyl polymer | 0.3 |
| Hydroxypropyl cellulose | 0.1 |
| 2-Aminomethylpropanol | 0.1 |
| Antiseptic | q.s. |
| Perfume | q.s. |
| Ion-exchanged water | q.s. |

(Preparation Method)

To ion-exchanged water were added propylene glycol, glycerol, ethyl alcohol, carboxyvinyl polymer, hydroxypropyl cellulose and 2-aminomethylpropanol. This mixture was adjusted to 70° C. by heating (aqueous phase).

Methyl phenyl polysiloxane, liquid paraffin, polyoxyethylene cetyl alcohol ether, an antiseptic, 2-hydroxy-4-methoxybenzophenone, lysophosphatidic acid and a perfume were mixed. This mixture was adjusted to 70° C. (oily phase).

Preparation Example 3: Milky lotion

| | wt. % |
|---|---|
| Cetyl alcohol | 1.0 |
| Beeswax | 0.5 |
| Vaseline | 2.0 |
| Squalane | 6.0 |
| Dimethyl polysiloxane | 2.0 |
| Ethyl alcohol | 5.0 |
| Glycerol | 4.0 |
| 1,3-Butylene glycol | 4.0 |
| Soybean lysolecithin (Reagent Lysolecithin; manufactured by Wako Pure Chemical Industries Ltd.) | 0.1 |
| Tranexamic acid | 1.0 |
| Polyoxyethylene (10) mono-oleate | 1.0 |
| Glycerol monostearate | 1.0 |
| Quince seed extract (5% aqueous solution) | 20.0 |
| Antiseptic | q.s. |
| Perfume | q.s. |
| Ion-exchanged water | q.s. |

(Preparation Method)

Glycerol and 1,3-butylene glycol were added to and mixed with ion-exchanged water. This mixture was adjusted to 70° C. by heating (aqueous phase). Cetyl alcohol, beeswax, vaseline, squalane, dimethyl polysiloxane, soybean lysolecithin, tranexamic acid, polyoxyethylene (10) mono-oleate, glycerol monostearate and an antiseptic were mixed. This mixture was adjusted to 70° C. by heating (oily phase). The aqueous phase was added to the oily phase so as to pre-emulsify this mixture. Then, quince seed extract and ethyl alcohol were added to the resulting emulsion, followed by stirring. After the emulsified particles were made uniform by means of a homomixer, the resulting emulsion was deaerated, filtered, and cooled to obtain a milky solution.

Preparation Example 4: Milky lotion

| | wt. % |
|---|---|
| Cetyl alcohol | 1.0 |
| Beeswax | 0.5 |
| Vaseline | 2.0 |
| Squalane | 6.0 |
| Dimethyl polysiloxane | 2.0 |
| Ethyl alcohol | 5.0 |
| Glycerol | 4.0 |
| 1,3-Butylene glycol | 4.0 |
| Soybean lysolecithin (LIPIDURE NC-22; manufactured by Nippon Oil & Fats Co., Ltd.) | 0.1 |
| Tranexamic acid | 1.0 |
| Polyoxyethylene (10) mono-oleate | 1.0 |
| Glycerol monostearate | 1.0 |
| Quince seed extract (5% aqueous solution) | 20.0 |
| Antiseptic | q.s. |
| Perfume | q.s. |
| Ion-exchanged water | q.s. |

(Preparation Method)

Glycerol and 1,3-butylene glycol were added to and mixed with ion-exchanged water. This mixture was adjusted to 70° C. by heating (aqueous phase). Cetyl alcohol, beeswax, vaseline, squalane, dimethyl polysiloxane, soybean lysolecithin, tranexamic acid, polyoxyethylene (10) mono-oleate, glycerol monostearate and an antiseptic were mixed. This mixture was adjusted to 70° C. by heating (oily phase). The aqueous phase was added to the oily phase so as to pre-emulsify this mixture. Then, quince seed extract and ethyl alcohol were added to the resulting emulsion, followed by stirring. After the emulsified particles were made uniform by means of a homomixer, the resulting emulsion was deaerated, filtered, and cooled to obtain a milky solution.

The aqueous phase was slowly added to the oily phase so as to pre-emulsify this mixture. After the emulsified particles were made uniform by means of a homomixer, the resulting emulsion was deaerated and cooled to obtain a cream.

Preparation Example 5: Cream

| | |
|---|---|
| Polyoxyethylene (20 mole addition) cetyl alcohol ether | 1.0 |
| Methyl phenyl polysiloxane (20 cs) | 2.0 |
| Liquid paraffin | 3.0 |
| 2-Hydroxy-4-methoxybenzophenone | 5.0 |
| Soybean saponin (Saponin, Prepared from Soybeans; manufactured by Wako Pure Chemical Industries Ltd.) | 0.2 |
| Propylene glycol | 5.0 |
| Glycerol | 2.0 |
| Ethyl alcohol | 15.0 |
| Carboxyvinyl polymer | 0.3 |
| Hydroxypropyl cellulose | 0.1 |
| 2-Aminomethylpropanol | 0.1 |
| Antiseptic | q.s. |
| Perfume | q.s. |
| Ion-exchanged water | q.s. |

(Preparation Method)

To ion-exchanged water were added propylene glycol, glycerol, ethyl alcohol, carboxyvinyl polymer, hydroxypropyl cellulose and 2-aminomethylpropanol. This mixture was adjusted to 70° C. by heating (aqueous phase).

Methyl phenyl polysiloxane, liquid paraffin, polyoxyethylene cetyl alcohol ether, an antiseptic, 2-hydroxy-4-methoxybenzophenone, soybean saponin and a perfume were mixed. This mixture was adjusted to 70° C. (oily phase).

The aqueous phase was slowly added to the oily phase so as to pre-emulsify this mixture. After the emulsified particles were made uniform by means of a homomixer, the resulting emulsion was deaerated and cooled to obtain a cream.

Preparation Example 6: Cream

| | |
|---|---|
| Polyoxyethylene (20 mole addition) cetyl alcohol ether | 1.0 |
| Methyl phenyl polysiloxane (20 cs) | 2.0 |
| Liquid paraffin | 3.0 |
| 2-Hydroxy-4-methoxybenzophenone | 5.0 |
| Soybean lecithin (Lecithin, Prepared from Soybeans; manufactured by Wako Pure Chemical Industries Ltd.) | 0.2 |
| Propylene glycol | 5.0 |
| Glycerol | 2.0 |
| Ethyl alcohol | 15.0 |
| Carboxyvinyl polymer | 0.3 |
| Hydroxypropyl cellulose | 0.1 |
| 2-Aminomethylpropanol | 0.1 |
| Antiseptic | q.s. |
| Perfume | q.s. |
| Ion-exchanged water | q.s. |

(Preparation Method)

To ion-exchanged water were added propylene glycol, glycerol, ethyl alcohol, carboxyvinyl polymer, hydroxypropyl cellulose and 2-aminomethylpropanol. This mixture was adjusted to 70° C. by heating (aqueous phase).

Methyl phenyl polysiloxane, liquid paraffin, polyoxyethylene cetyl alcohol ether, an antiseptic, 2-hydroxy-4-methoxybenzophenone, lysophosphatidic acid and a perfume were mixed. This mixture was adjusted to 70° C. (oily phase).

The aqueous phase was slowly added to the oily phase so as to pre-emulsify this mixture. After the emulsified particles were made uniform by means of a homomixer, the resulting emulsion was deaerated and cooled to obtain a cream.

INDUSTRIAL APPLICABILITY

Since the lysophospholipids and soybean-derived preparations in accordance with the present invention can promote the production of laminin 5 in epidermic cells, compositions containing them as active ingredients and their use can be utilized especially in the fields of cosmetics and dermatology.

What is claimed is:

1. A method for potentiating epidermic cells of a mammal which comprises administering a compound of the following formula (I) or a mixture of two or more of such compounds to the mammal in an amount sufficient to promote the production of laminin 5 in epidermic cells:

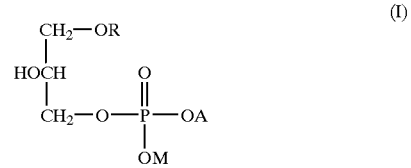

wherein R is a $C_{19\text{-}22}$ fatty acid residue optionally having up to six unsaturated double bonds, A is a hydrogen atom or a $-CH_2CH_2N^+(CH_3)_3$ group, and M is a hydrogen atom or an alkali metal atom, but is a hydrogen atom when A is a $-CH_2CH_2N^+(CH_3)_3$ group.

2. A method for potentiating epidermic cells of a mammal which comprises administering a preparation derived from soybeans to the mammal in an amount sufficient to promote the production of laminin 5 in epidermic cells, wherein the preparation derived from soybeans is an organic solvent extract fraction containing both a soybean saponin fraction and a soybean lecithin fraction derived from soybeans and having an activity for promoting the production of laminin 5 in human keratinized epidermic cells.

3. A method for potentiating epidermic cells of a mammal which comprises administering a preparation derived from soybeans to the mammal in an amount sufficient to promote the production of laminin 5 in epidermic cells, wherein the preparation derived from soybeans is an organic solvent extract fraction containing a soybean lecithin fraction derived from soybeans and having an activity for promoting the production of laminin 5 in human keratinized epidermic cells, with the proviso that the preparation does not contain a soybean saponin fraction.

* * * * *